(12) United States Patent
Chau et al.

(10) Patent No.: US 7,476,635 B2
(45) Date of Patent: *Jan. 13, 2009

(54) PROCESS FOR MAKING SUPPORTED THIN ZEOLITE MEMBRANE

(75) Inventors: Christophe Chau, Rueil Malmaison (FR); Michaeel Sicard, Palaiseau (FR); Ronan Le Dred, Riedisheim (FR)

(73) Assignee: Institut Francais Du Petrole, Rueil Malmaison Cedex (FR)

( * ) Notice: Subject to any disclaimer, the term of this patent is extended or adjusted under 35 U.S.C. 154(b) by 945 days.

This patent is subject to a terminal disclaimer.

(21) Appl. No.: 10/667,654

(22) Filed: Sep. 23, 2003

(65) Prior Publication Data

US 2004/0058799 A1 Mar. 25, 2004

Related U.S. Application Data

(63) Continuation-in-part of application No. 10/453,867, filed on Jun. 3, 2003, now abandoned.

(30) Foreign Application Priority Data

Jun. 3, 2002 (FR) .................................. 02 06818

(51) Int. Cl.
*B01D 61/00* (2006.01)
(52) U.S. Cl. ................................ 502/4; 502/64; 502/70
(58) Field of Classification Search ...................... 502/4, 502/64, 70
See application file for complete search history.

(56) References Cited

U.S. PATENT DOCUMENTS

| | | | |
|---|---|---|---|
| 5,464,798 A * | 11/1995 | Jia et al. ........................ | 502/64 |
| 5,567,664 A * | 10/1996 | Barri et al. ..................... | 502/4 |
| 5,871,650 A | 2/1999 | Lai et al. | |
| 5,968,366 A * | 10/1999 | Deckman et al. ............. | 210/651 |
| 6,074,457 A * | 6/2000 | Anthonis et al. ............... | 95/45 |
| 6,090,289 A | 7/2000 | Verduijn et al. | |
| 6,140,263 A * | 10/2000 | Anstett et al. .................. | 502/4 |
| 6,197,427 B1 * | 3/2001 | Anstett et al. ................ | 428/426 |
| 6,440,885 B1 * | 8/2002 | Pierotti et al. .................. | 502/4 |
| 6,582,495 B2 * | 6/2003 | Chau et al. ..................... | 95/45 |
| 6,734,129 B2 * | 5/2004 | Lai et al. ........................ | 502/4 |
| 6,818,333 B2 * | 11/2004 | Chau et al. .................. | 428/702 |
| 2001/0012505 A1 | 8/2001 | Matsukata | |

OTHER PUBLICATIONS

Vroon, et al., "Transport properties of alkanes throught ceramic thin zeolite MFI membranes," J. Membr. Sci., 113, pp. 293-300, 1996, no month.*

* cited by examiner

*Primary Examiner*—Steven Bos
(74) *Attorney, Agent, or Firm*—Millen, White, Zelano, & Branigan, P.C.

(57) ABSTRACT

Described is a process for the preparation of a supported zeolite membrane that consists of a zeolite/substrate composite layer, whose zeolite phase exhibits a crystallinity of at least 85%, comprising:
a) the formation of a gel or a solution that comprises at least one source of silica and water, supplemented with at least one polar organic compound,
b) bringing into contact said gel or said solution with a porous substrate,
c) the crystallization of the zeolite starting from said gel or said solution; and
d) the elimination of residual agents.

The molar ratio of the water to the silica in the gel or the solution in stage a) is between 27:1 and 35:1. The crystallization time of stage c) is at least 25 hours.

Said process is particularly suited for the preparation of zeolite membranes whose zeolite phase is of the MFI-structural type.

13 Claims, No Drawings

PROCESS FOR MAKING SUPPORTED THIN ZEOLITE MEMBRANE

This application is a continuation-in-part of application Ser. No. 10/453,867 filed Jun. 3, 2003 and is related to Applicants' concurrently filed application entitled "Thin Zeolite Membrane, Its Preparation And Its Use In Separation" filed on Jun. 3, 2003; Ser. No. 10/452,940, and claims priority of French application 02/06.818 filed Jun. 3, 2002.

This invention relates to the field of supported zeolite membranes that are used in separation.

More particularly, it has as its object a process for controlled preparation of a supported zeolite membrane, the zeolite membranes that are obtained by this process and their use in separation.

Various processes for developing zeolite membranes have already been described. To date, it appears difficult to obtain in a controlled and reproducible manner zeolite membranes whose layer that contains the zeolite is continuous and thin. The thinness and the continuity of such a layer are essential parameters for obtaining a membrane material that exhibits advantageous properties that can be used in industrial separation processes. In particular, it is particularly difficult to control the preparation of zeolite membranes: the production processes involve several stages, and it is often necessary to reproduce the crystallization stage on several occasions to obtain, following stages that are time-intensive, high in operating costs, chemical products and energy, a continuous layer that can be used in separation. Furthermore, the thermal and mechanical stability of these inorganic membranes is crucial. Actually, the inorganic materials can in general be used at relatively high temperatures, for example higher than the organic polymer membranes that generally operate at a temperature of less than 100° C. It is then essential, for an industrial and commercial application, to use a membrane that can remain stable during operations and uses at high temperatures, and even high pressures. The hydrothermal path that involves porous substrates exhibits the advantage of stabilizing the zeolite crystals in the pores of a porous matrix (alumina, stainless steel, for example) and also on the surface of the latter.

In Patent Application EP-A-0 778 075, a process for developing zeolite membranes that are supported by porous glass is described. U.S. Pat. No. 5,429,743 and International Patent Application WO-A-95/29751 describe operating procedures for obtaining composite membranes that are supported by an inorganic macroporous matrix. Reference can also be made to documents U.S. Pat. No. 4,099,692, WO-A-93/19840, U.S. Pat No. 5,567,664 and WO-A-96/01683. In International Patent Application WO-A-00/33948, a process for obtaining composite membranes of zeolite supported on optionally multi-channel tubular solids is described. All of these composite membrane materials with a zeolite base are formed by a zeolite phase that is deposited on a substrate. A series of recent patents (U.S. Pat. Nos. 5,871,650, 5,968,366, 6,090,289, 6,074,457, WO-A-00/53297, WO-A-00/53298) describes the preparation of zeolite membranes whose MFI-structural type zeolite phase is found on the outside surface of a porous substrate. A drawback of the membranes according to the prior art is that they generally have texture defects, inadequate crystallinity and/or the presence of (an) amorphous zone(s) that has a negative effect on the performance levels of the molecular separation and in particular on the selectivity. The presence of empty voids between the zeolite crystals and/or the presence of an amorphous phase significantly alters the selectivity of the separation.

The crystallization of the zeolite is generally carried out by multiple hydrothermal treatments of a mixture that contains the precursors of the zeolite phase, which increases the effective thickness of the separating layer. When the crystallization stage of the zeolite is reproduced on several occasions, the synthesis is reproduced after an optional return of the material to ambient temperature, washing and drying of said material. The repetition and the succession of identical operations for the preparation of zeolite membranes allow the deposition of successive layers and/or the formation of zeolite crystals that fill the interparticulate spaces, which allows the production of a continuous layer for the separation. This method of synthesis in several stages, if it leads to the production of a continuous layer, also leads to the production of thick zeolite layers that run the risk of cracking during the calcination of the membrane (Vroon, Z. A. E. P., Keizer, K., Burggraaf, A. J., Verweij, H., *J. Membr. Sci.* 144 (1998) 65-76) from bringing the membrane separation unit into steady operation or from use at high temperature. Furthermore, the increase in thickness can considerably limit the transfer of material through the membrane during the separation operation and thus can reduce the technical and economical advantage of the separation operation by membrane, due to a reduction in productivity of said separation stage. In addition, a membrane whose separating layer is thick requires using large surfaces of said membrane material to treat a flow of feedstock of the mixture to be separated, which is reflected by high investments. In addition, this method of synthesis in several stages requires a large amount of precursors of the zeolite phase, which increases in particular the cost of raw materials and precursors used. It also exhibits the drawback of extending the period for obtaining the membrane material and increasing the operating cost of the separation.

One of the difficulties linked to the preparation of zeolite-based membranes resides in particular in the monitoring of the crystallization of the zeolite so as to obtain zeolite crystals that are well linked to the substrate, located primarily in the pores of the substrate, thus forming a continuous and thin zeolite/substrate composite layer (obtained by obstructing the empty voids of the substrate by zeolite phase crystals) so as to limit the resistance of transfer through the membrane material. Placing most, and preferably all, of the zeolite phase in the pores of the substrate imparts very good thermal and mechanical resistance to the membrane material. It cannot be ruled out, however, that a minority portion of the zeolite phase be located on the outside surface of the substrate.

One of the objects of this invention is to provide a process that allows the development of supported zeolite membranes that comprise a continuous and thin zeolite/substrate composite layer in which the zeolite phase that is crystallized by a single hydrothermal treatment exhibits the characteristics set forth above. In particular, said zeolite phase, which is active in separation, i.e., selective compared to the compounds to be separated, is thin (like the resulting zeolite/substrate composite layer that exhibits a thickness of less than 2 μm, preferably less than 1 μm, and very preferably less than 0.5 μm) and also exhibits a high crystallinity. Thus, the amount of non-zeolite solid that is formed remains very low and very much in the minority compared to the amount of the zeolite phase, and the resulting membrane consequently exhibits high separating qualities, which is reflected by very high separation performance levels. In particular, the selectivity or separating power of the membranes that are prepared according to the process of the invention is very high. Furthermore, these membranes are composite materials, whose separating layer is formed by zeolite crystals that are immobilized and stabilized in the pores of an inorganic substrate. These zeolite membranes also exhibit a very good structural integrity, i.e., an absence of defects in the structure of the composite layer and an absence of interparticulate spaces, i.e., voids that are present between the crystals of the zeolite, which is difficult to obtain by the prior processes in a single stage.

According to the invention, the process for preparation of a supported zeolite membrane comprising a zeolite/substrate composite layer, whose zeolite phase exhibits a crystallinity of at least 85%, comprises:

a) the formation of a gel or a solution that comprises at least one source of silica and water, supplemented with at least one polar organic compound,
b) bringing into contact said gel or said solution with a porous substrate,
c) the crystallization of the zeolite starting from said gel or said solution, and
d) the elimination of residual agents, whereby said process is characterized in that the molar ratio of the water to the silica $H_2O/SiO_2$ in said gel or said solution in stage (a) is 27:1 to 35:1, and the crystallization time in stage (c) is at least 25 hours.

The crystallinity of the zeolite phase represents the relative amount of the zeolite phase that is crystallized relative to the solid that is formed at the end of the hydrothermal treatment. Thus, a crystallinity of at least 85% signifies that at least 85% by weight of solid that is formed at the end of the hydrothermal treatment is of zeolite type, identifiable by DRX analysis, whereby the non-zeolite portion, without a separating property, represents less than 15% by weight of solid that is formed at the end of the hydrothermal treatment. More particularly, a crystallinity of 100% therefore signifies the production of a zeolite membrane that exhibits 100% of quantity relative to the crystallized zeolite and the absence of any amorphous or solid phase without separation properties. According to the invention, the thin zeolite phase of the zeolite membrane advantageously exhibits a crystallinity of at least 90%.

The molar ratio of the water to the silica $H_2O/SiO_2$ in said gel or said solution in stage (a) is preferably 27:1 to 32:1. Advantageously, stage (a) of the process according to the invention is carried out by using the molar ratios of the water to the silica in said gel or said solution of 28:1 to 31:1.

The silica source that is used in stage (a) of the process according to the invention is preferably a colloidal silica or a precipitated silica. These can also be silicate ions such as sodium silicate, silicon alkoxides or silicon tetrachloride.

Other elements can also be introduced in a minority amount during stage (a) of the process according to the invention. In particular, aluminum, boron, gallium, germanium, titanium, and phosphorus as well as the mixture of these elements can be added during stage (a).

According to the invention, the polar organic compound that is supplemented with gel or the solution that comprises at least said source of silica and water is preferably a basic compound. These are advantageously organic hydroxides, such as tetrapropylammonium hydroxide, organic structuring agents that contain ionic pairs (ammonium or phosphonium ions and the corresponding anions) or neutral molecules (amines, alcohols or ethers such as crown ethers and cryptands). The molar ratio of the polar organic compound to the silica is between 0.3:1 and 0.6:1 and preferably between 0.35:1 and 0.50:1. The hydroxide ions or fluoride ions can be used, furthermore, for the dissolution of the precursors and are introduced into the preparation medium, for example, in the form of sodium hydroxide, organic hydroxides and hydrofluoric acid.

The porous substrate that is used in stage b) of the process according to the invention preferably consists of an inorganic material. A ceramic substrate with an alumina and/or zirconia and/or titanium oxide base is a suitable substrate. Other materials, of the type indicated below, may also be suitable: carbon, silica, zeolites, clays, glass, and metal (stainless steel, silver). The use of an alumina substrate of the alpha- or gamma-allotropic variety is preferred. All of the geometries may be suitable for the substrate, and the latter may be, for example, tubular, flat, in the form of disks, sheets or else fibers, in particular hollow fibers whose surface area/volume ratio (compactness) is high.

Advantageously, the crystallization time in the zeolite in stage (c) is at least 40 hours, and even more advantageously, it is at least 65 hours. According to the invention, the crystallization of the zeolite is generally carried out in a single stage, i.e., the zeolite is generally crystallized by a single hydrothermal treatment. The range of temperatures for the hydrothermal crystallization step is 100-250° C. and the preferred range is 150-210° C.

The elimination of the residual agents, primarily the polar organic compound, according to stage (d) of the process according to the invention, is carried out by heat treatment that is carried out between 350 and 550° C., preferably between 400° C. and 500° C., in a furnace under an atmosphere of air or under an atmosphere of $N_2/O_2$ in variable proportions. After eliminating these residual agents, the micropores of the zeolite membranes can then be used for a separation operation.

The process according to the invention is particularly suited for the preparation of zeolite membranes of which the zeolite phase is of the MFI-structural type.

The invention also relates to the supported zeolite membranes that are obtained by the process of the invention, in which the zeolite phase exhibits a crystallinity of at least 85%, preferably at least 90%, whereby said phase is thin and located primarily, preferably as a whole, in the pores of said substrate. Said membranes exhibit, in the n-butane/isobutane separation, an n-butane permeance of at least $3.10^{-7}$ mol/$m^2$.s.Pa at the temperature of 180° C.

Recall that the permeance of a gas, expressed in mol/$m^2$.s.Pa, is, by definition, the molar flow rate of this gas related to the unit membrane surface area and related to the partial-pressure difference of this gas between the upstream (where the feedstock circulates) and the downstream (where the permeate is recovered). The permeance of a gas is therefore the molar flow rate of this gas that passes through the membrane per unit of surface area and pressure. Selectivity $\alpha$ (called permselectivity) is, in the case of measurements of permeation of pure elements, the ratio of the permeances of these pure elements, i.e., within the scope of this invention, the ratio of the permeances of n-butane and isobutane.

The zeolite membranes that are obtained by the process of the invention can be used for different separations. They are advantageously used in gas separation processes, vapor separation processes and liquid separation processes. They are thus preferably used for separating:

linear and branched paraffins (n- and iso-paraffins), such as, for example, n-butane and isobutane,
paraffins that are branched among them (mono-branched and di-branched or multi-branched),
linear and branched olefins (n- and iso-olefins),
paraffins and olefins,
naphthenes and paraffins,
paraffins and aromatic compounds,
hydrogen and hydrocarbons; for example in mixtures that contain the hydrogen and hydrocarbons below, present separately or simultaneously, light paraffins such as methane, ethane, propane or butane and isobutane; or else hydrogen, and light olefins such as ethylene, propylene and isomers of butenes, isobutene; or else hydrogen and polyunsaturated hydrocarbons such as acetylene, propyne, butyne and butadiene, whereby these hydrocarbons are taken separately with hydrogen or in a mixture, isomers of xylene (ortho-, meta-, and para-xylenes), methane and $CO_2$ According to the invention, the quality and the properties of molecular sieving of the zeolite phase are used to separate molecules whose dimensions are strictly less than, on the one hand, and strictly larger than, on the other hand, those of the pores of the zeolite (separation by size differentiation). By way of illustration, in the case of the MFI zeolite that has a mean pore size of 0.55 nm (channel dimensions of 0.51*0.55 and 0.53*0.56 $nm^2$), the zeolite membranes that are obtained by the process of the invention can advantageously be used for the separation of molecules, in particular containing carbon and hydrogen atoms, whose dimensions are, on the one hand, less than approximately 0.45 nm and, on the other hand, larger than 0.55 nm. Furthermore, the interactions between the molecules to be separated and the zeolite phase of the membrane can also be used to carry out the separation of said molecules (separation by adsorption).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

Preparation of Zeolite Membranes (According to the Invention)

Sections or elements of a porous alumina tube (of an alpha-allotropic variety, provided by the Exekia Company) are used as a substrate for the formation of zeolite membranes whose zeolite phase is of the MFI-structural type. These tubular elements are immersed in a precursor solution of the MFI zeolite. This solution accepts 1 $SiO_2$:0.4 TPAOH:27.0$H_2O$ for molar stoichiometry. It is obtained by mixing Aerosil 380®-type silica (provided by the Degussa Company) and a molar solution of tetrapropyl ammonium hydroxide TPAOH (marketed by the Fluka Company) at ambient temperature. The substrate and solution elements are placed in a horizontal autoclave at 175° C. while being rotated. These substrate elements, of about 2.5 cm in length, are withdrawn after a crystallization time (dwell time) of 72 hours in the autoclave. They are successively washed with distilled water and dried at 60° C. The polar organic compound is eliminated by heat treatment at 480° C.

The phase analysis by x-ray diffraction on this zeolite membrane that is obtained after 72 hours of dwell time in an autoclave confirms the presence of MFI zeolite crystals that are located in the pores of the alpha-alumina substrate.

The preparation procedure described above is repeated on three occasions by varying for each preparation the amount of water that is introduced for the formation of each of the zeolite precursor solutions. Three new membranes are thus prepared according to the invention for which the solution, precursor of the MFI zeolite, respectively accepts 1 $SiO_2$:0.4 TPAOH:28.0$H_2O$, 1 $SiO_2$:0.4 TPAOH: 29.7$H_2O$ and 1 $SiO_2$: 0.4 TPAOH:31.5$H_2O$ for molar stoichiometry. The phase analysis by x-ray diffraction on these three membranes obtained after 72 hours of dwell time in an autoclave confirms the presence of MFI zeolite crystals that are located in the pores of the alpha-alumina substrate.

The results are summarized in Table 1.

TABLE 1

| $H_2O/SiO_2$ Molar Ratio | 27.0 | 28.0 | 29.7 | 31.5 |
|---|---|---|---|---|
| Crystallinity (%) | 85 | 87 | 93 | 85 |

For values of the $H_2O/SiO_2$ molar ratio included in the interval that characterizes the invention, the zeolite membranes exhibit a crystallinity of at least 85%. The maximum crystallinity is obtained for an $H_2O/SiO_2$ molar ratio that is equal to 29.7. The majority of the zeolite membranes that are prepared according to the process of the invention are formed by the zeolite phase, which necessarily leads to very satisfactory separation performance levels (see Example 4).

EXAMPLE 2

Preparation of Zeolite Membranes (Not in Accordance With the Invention)

The operating procedure that is described in Example 1 is adopted, modifying only the amount of water that is introduced into the solution, precursor of the MFI zeolite. The silica source is Aerosil 380®. The crystallization time is 72 hours, and the elimination of the tetrapropyl ammonium hydroxide TPAOH is carried out at 480° C.

Four zeolite membrane preparations are thus initiated for which the solution, precursor of the MFI zeolite, respectively accepts 1 $SiO_2$:0.4 TPAOH: 18.3$H_2O$: 1 $SiO_2$:0.4TPAOH: 22.8$H_2O$; 1 $SiO_2$:0.4 TPAOH:41.2$H_2O$ and 1 $SiO_2$:0.4 TPAOH:63.7$H_2O$ for molar stoichiometry. The phase analysis by x-ray diffraction on these four membranes that are obtained after 72 hours of dwell time in an autoclave confirms the presence of MFI zeolite crystals that are located in the pores of the alpha-alumina substrate.

The results are summarized in Table 2.

TABLE 2

| $H_2O/SiO_2$ Molar Ratio | 18.3 | 22.8 | 41.2 | 63.7 |
|---|---|---|---|---|
| Crystallinity (%) | 73 | 79 | 77 | 76 |

By comparison of the results that are presented in Tables 1 and 2, it appears that for the molar ratios beyond the interval that characterizes the invention, the zeolite membranes that are obtained have a less favorable crystallinity than those obtained by a process in which the $H_2O/SiO_2$ molar ratio is included in the interval that characterizes the invention. The membranes that are prepared according to Example 2 contain an amorphous phase without a separating property in much larger proportion than those that are prepared according to the process of the invention (Example 1).

EXAMPLE 3

Preparation of Zeolite Membranes (According to the Invention)

Influence of the Silica Source Used:

The preparation procedure is analogous to the one that is described in Example 1, but the preparation is conducted in the presence of a silica source that is separate from the one used in Example 1. The silica source Bindzil 40/130® in colloidal form (marketed by the Akzo Nobel Company) is used to prepare four membranes from four different solutions whose stoichiometry is 1 $SiO_2$:0.4 TPAOH:$xH_2O$ with x=28.0; 29.7; 31.5 and 34.5. The crystallization time is 72 hours, and the elimination of the tetrapropyl ammonium hydroxide TPAOH is carried out at 480° C. The phase analysis by x-ray diffraction on these four membranes that are obtained after 72 hours of dwell time in an autoclave confirms the presence of MFI zeolite crystals that are located in the pores of the alpha-alumina substrate.

The results are summarized in Table 3.

TABLE 3

| H2O/SiO2 Molar Ratio | 28.0 | 29.7 | 31.5 | 34.5 |
|---|---|---|---|---|
| Crystallinity (%) | 91 | 99 | 94 | 90 |

This example confirms the positive effect, already shown in Example 1, of the $H_2O/SiO_2$ molar ratio, when the latter is between 27 and 35. The zeolite membranes that are obtained in this Example 3 have a very high crystallinity, with a maximum value of 99% for an $H_2O/SiO_2$ molar ratio that is equal to 29.7. The silica source that is used for the formation of the solution, precursor of the MFI zeolite, does not have a significant influence on the final membrane material when the $H_2O/SiO_2$ molar ratio is between 27 and 35.

EXAMPLE 4

Separation Properties of Membranes Prepared According to the Process of the Invention Two membranes that are referenced A and B are prepared from a stoichiometric solution of $H_2O/SiO_2$ that is equal to 29.7 and from alpha-alumina tubes with a length of 15 cm (active separation surface of 20.4 cm²). The operating procedure is identical to the one that is described in Example 1: the silica source is Aerosil 380®, the crystallization time is 72 hours, and the heat treatment to eliminate the organic compound is carried out at 480° C. The zeolite phase is of the MFI-structural type.

Gas separation measurements (gaseous permeation) are carried out at 180° C. on the thus prepared membranes so as to characterize the properties and the structural quality, whereby the gases to be separated among them are n-butane and isobutane.

To do this, each membrane is inserted into a permeating device (permeation measurement module) with carbon joints that keep the measurement module sealed. The unit (module/membrane) is placed in a gaseous permeation unit, and the material is treated in advance at 350° C. under a flow of helium (cover gas) that makes it possible to eliminate all traces of adsorbable gas on the outside surface and in the inside pores of the membrane material. During the gas permeation measurements, the membrane is subjected to a difference in pressure, the pressure of the upstream side where the feedstock (in this example n-butane n-$C_4H_{10}$ or the pure isobutane I—$C_4H_{10}$) circulates is kept constant at 1.5 bar (0.15 MPa) absolute and the pressure of the downstream side, where the permeate is recovered after selective extraction of a portion of the molecules that are present in the feedstock, is the atmospheric pressure. This pressure difference constitutes the driving force of the transfer through the membrane. The gas flow that passes through the membrane is measured with a volumetric flowmeter. The detection threshold is less than 0.002 ml/mn or about $10^{-6}$ mol/m².s of n-butane or isobutane.

The measurement of the gas flows passing through the membrane is carried out with pure n-butane and isobutane. These molecules exhibit the advantage of having kinetic diameters (0.43 nm for n-butane and 0.49 nm for isobutane) that are very close to the mean dimensions of the opening of pores of the MFI zeolite (0.55 nm). It should be noted that with the selection of these sampler molecules that are n-butane and isobutane, this method of characterization is considered to be a very strict and very selective criterion for characterizing microporous inorganic membranes such as the MFI-structural type zeolites. It consequently allows the demonstration of the presence of any discontinuity, defects, or cracks in the zeolite/substrate composite layer. Conversely, the absence of significant defects in the membrane reveals a very high separation potential. In particular, this characterization method that uses n-butane and isobutane is very strict relative to other characterization tests that are used in the prior art, for example the tests using the pairs $N_2/SF_6$, $H_2/n-C_4$ or $H_2/i-C_4$.

Membranes A and B then exhibit, at the end of the characterization measurements, permeances of 3.18 and $3.05.10^{-7}$ mol/m².s.Pa of n-butane at the temperature of 180° C. Under the same conditions, these materials are impermeable to isobutane. As a result, the n-butane/isobutane selectivity reaches infinite values. These separation performance levels are particularly high and demonstrate the total absence of defects in the zeolite/substrate composite layer as well as the thinness and the continuity of said layer. By comparison, it is generally admitted in the literature that the MFI-type membranes exhibit good textural integrity, i.e., an absence of mesopore- and macropore-type structural defects, when the n-butane/isobutane selectivity is higher than 10 (Vroon et al., J. Membr. Sci. 113 (1996) 293,).

The preceding examples can be repeated with similar success by substituting the generically or specifically described reactants and/or operating conditions of this invention for those used in the preceding examples.

The entire disclosures of all applications, patents and publications, cited herein and of corresponding French application No. 02/06.818, filed Jun. 3, 2002 is incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the preparation of a supported zeolite membrane comprising a zeolite/substrate composite layer, whose zeolite phase exhibits a crystallinity of at least 85%, wherein said process comprises:

a) forming of a gel or a solution that comprises at least one source of silica and water, supplemented with at least one polar organic compound;
b) bringing into contact said gel or said solution with a porous substrate;
c) crystallizing zeolite starting from said gel or said solution; and
d) elimination of residual agents, characterized in that, in (a), the molar ratio of water to silica in said gel or said solution is 27:1 to 35:1 and wherein in (c), the crystallization is conducted in a single hydrothermal treatment for at least 25 hours at a temperature of 100-250° C.

2. A process according to claim 1, wherein in (a), the molar ratio of the water to the silica in said gel or said solution is between 27:1 and 32:1.

3. A process according to claim 1, wherein in (a), the molar ratio of the water to the silica in said gel or said solution is between 28:1 and 31:1.

4. A process according to claim 1, wherein in (c), the crystallization time is at least 65 hours.

5. A process according to claim 1, wherein the zeolite phase exhibits a crystallinity of at least 90%.

6. A process according to claim 1, wherein in (a), the molar ratio of the polar organic compound to the silica is between 0.3:1 and 0.6:1.

7. A process according to claim 1, wherein the porous substrate comprises: ceramic based on alumina and/or zirconia and/or titanium oxide, carbon, silica, zeolites, clays, glass or metal.

8. A process according to claim 1, wherein the zeolite phase is a zeolite MFI-structure.

9. A process according to claim 1, wherein said at least one polar organic compound is selected from the group consisting of organic hydroxides, organic structuring agents containing ammonium or phosphonium ions and corresponding anions, amines, alcohols, crown ethers and cryptands.

10. A process according to claim 1, wherein the water to the silica in said gel or said solution is between 28:1 and 31:1; crystallization is conducted for at least 65 hours; the zeolite phase exhibits a crystallinity of at least 90%; the molar ratio of the polar organic compound to the silica is between 0.3:1 and 0.6:1; and the zeolite phase is a zeolite having MFI-structure.

11. A process according to claim 1, wherein crystallization is conducted at a temperature of 150-210° C.

12. A process according to claim 4, wherein crystallization is conducted at a temperature of 150-210° C.

13. A process according to claim 1, wherein the zeolite membrane has a thickness of less than 0.5 μm.

* * * * *